(12) United States Patent
Tang et al.

(10) Patent No.: US 11,301,999 B2
(45) Date of Patent: Apr. 12, 2022

(54) SHAPE-AWARE ORGAN SEGMENTATION BY PREDICTING SIGNED DISTANCE MAPS

(71) Applicant: TENCENT AMERICA LLC, Palo Alto, CA (US)

(72) Inventors: Hui Tang, Mountain View, CA (US); Chao Huang, Palo Alto, CA (US); Shih-Yao Lin, Palo Alto, CA (US); Zhen Qian, Santa Clara, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 140 days.

(21) Appl. No.: 16/869,012

(22) Filed: May 7, 2020

(65) Prior Publication Data
US 2021/0350528 A1    Nov. 11, 2021

(51) Int. Cl.
*G06T 7/00*   (2017.01)
*G06N 3/08*   (2006.01)
*G06N 3/04*   (2006.01)
*G06T 5/00*   (2006.01)
*G06T 5/50*   (2006.01)
*G06T 7/174*  (2017.01)
*G06F 17/17*  (2006.01)

(52) U.S. Cl.
CPC .............. *G06T 7/0012* (2013.01); *G06N 3/04* (2013.01); *G06N 3/08* (2013.01); *G06T 5/002* (2013.01); *G06T 5/50* (2013.01); *G06T 7/174* (2017.01); *G06F 17/17* (2013.01); *G06T 2207/10081* (2013.01); *G06T 2207/20081* (2013.01); *G06T 2207/20084* (2013.01); *G06T 2207/20182* (2013.01)

(58) Field of Classification Search
None
See application file for complete search history.

(56) References Cited

U.S. PATENT DOCUMENTS

| | | | |
|---|---|---|---|
| 10,984,530 B1 * | 4/2021 | Yao | G06T 7/38 |
| 11,030,747 B1 * | 6/2021 | Feng | A61N 5/1039 |
| 2008/0181479 A1 * | 7/2008 | Yang | A61B 8/0883 |
| | | | 382/131 |
| 2011/0123095 A1 * | 5/2011 | Florin | G06T 7/143 |
| | | | 382/154 |
| 2017/0270664 A1 * | 9/2017 | Hoogi | A61B 6/5217 |

(Continued)

OTHER PUBLICATIONS

Xue, Yuan et al. "Shape-Aware Organ Segmentation by Predicting Signed Distance Maps." arXiv:1912.03849v1 [cs.CV] Dec. 9, 2019 (Year: 2019).*

(Continued)

*Primary Examiner* — Jiangeng Sun
(74) *Attorney, Agent, or Firm* — Sughrue Mion, PLLC

(57) ABSTRACT

A computer-implemented method of training a neural network for organ segmentation may be provided. The method may include: collecting a set of digital sample images from a database; inputting the collected set of digital images into a neural network recognition model; and training the neural network recognition model to recognize a first object in a first digital image as a specific object based on the first object being similar to a second object in a second digital image. The method may comprise predicting a signed distance map (SDM) in conjunction with a segmentation map.

19 Claims, 7 Drawing Sheets

(56) References Cited

U.S. PATENT DOCUMENTS

| | | | |
|---|---|---|---|
| 2019/0015059 A1* | 1/2019 | Itu | A61B 6/502 |
| 2019/0030370 A1* | 1/2019 | Hibbard | A61N 5/1045 |
| 2019/0192880 A1* | 6/2019 | Hibbard | A61N 5/1039 |
| 2020/0034948 A1* | 1/2020 | Park | A61N 5/1039 |
| 2021/0074000 A1* | 3/2021 | Wong | G06T 7/11 |

OTHER PUBLICATIONS

Al Scher et al., "Hippocampal shape analysis in Alzheimer's disease: a population-based study", Neuroimage, 2007, vol. 36, Issue 1, pp. 8-18, Abstract Only (2 pages total).

Kevin L Moore et al., "Experience-based quality control of clinical intensity-modulated radiotherapy planning", Int J Radiat Oncol Biol Phys., 2011, vol. 81, Issue 2, pp. 545-551, Abstract Only (2 pages total).

Michael Kass et al., "Snakes: Active Contour Models", International Journal of Computer Vision, 1988, pp. 321-331 (11 pages total).

Stanley Osher et al., Fronts Propagating with Curvature Dependent Speed:Algorithms Based on Hamilton-Jacobi Formulations, Journal of Computational Physics, 1988, vol. 79, pp. 12-49 (38 pages total).

Juan J. Cerrolaza et al., "Automatic Multi-Resolution Shape Modeling of Multi-Organ Structures", Med Image Anal., 2015, vol. 25, No. 1, pp. 1-28 (28 pages total).

P. Aljabar et al., "Multi-atlas based segmentation of brain images: atlas selection and its effect on accuracy", Neuroimage, 2009, vol. 46, No. 3, pp. 726-738, Abstract Only (1 page total).

Olaf Ronneberger et al., "U-Net: Convolutional Networks for Biomedical Image Segmentation", Pattern Recognition and Image Processing, 2015, arXiv:1505.04597v1, pp. 1-8 (8 pages total).

Ozgun Cicek et al., "3D U-Net: Learning Dense Volumetric Segmentation from Sparse Annotation", Pattern Recognition and Image Processing, 2016, arXiv:1606.06650v1, pp. 1-8 (8 pages total).

Konstantinos Kamnitsas et al., "Efficient Multi-Scale 3D CNN with fully connected CRF for Accurate Brain Lesion Segmentation", 2017, arXiv:1603.05959v3, pp. 1-49 (49 pages total).

Timo Kohlberger et al., "Automatic multi-organ segmentation using learning-based segmentation and level set optimization", ResearchGate, 2011, pp. 338-345 (9 pages total).

Samunda Perera et al., "Motion Segmentation of Truncated Signed Distance Function based Volumetric Surfaces", IEEE, 2015 (8 pages total).

Ping Hu et al., "Deep Level Sets for Salient Object Detection", Proceedings of the IEEE Conference on Computer Vision and Pattern Recognition (CVPR), 2017, pp. 2300-2309 (10 pages total).

Jeong Joon Park et al., "DeepSDF: Learning Continuous Signed Distance for Shape Representation", Proceedings of the IEEE/CVF Conference on Computer Vision and Pattern Recognition (CVPR), 2019, pp. 1-19 (19 pages total).

S. M. Masudur Rahman Al Arif et al., "SPNet: Shape Prediction using a Fully Convolutional Neural Network", MICCAI, 2018 (8 pages total).

Shusil Dangi et al., "A Distance Map Regularized CNN for Cardiac Cine MR Image Segmentation", The International Journal of Medical Physcis Research and Practice, 2019, vol. 46, Issue 12, arXiv:1901.01238v2, pp. 1-11 (16 pages total).

Fernando Navarro et al., "Shape-Aware Complementary-Task Learning for Multi-Organ Segmentation", MLMI, 2019, arXiv:1908.05099v1, pp. 1-8 (8 pages total).

Yuxin Wu et al., "Group Normalization", Facebook AI Research (FAIR), 2018, arXiv:1803.08494v3, pp. 1-10 (10 pages total).

International Search Report dated May 24, 2021 in International Application No. PCT/US21/20836.

Written Opinion of the International Searching Authority dated May 24, 2021 in International Application No. PCT/US21/20836.

Yuan Xue et al., "Shape-Aware Organ Segmentation by Predicting Signed Distance Maps", 2019, arXiv:1912.03849v1 (8 pages total).

* cited by examiner $$\mathcal{L}_{\text{product}} = -\sum_{t=1}^{C} \frac{y_t p_t}{(y_t p_t + p_t^2 + y_t^2)}$$

FIG. 4A $$\mathcal{L}_{\text{Dice}} = N - \sum_{t=1}^{N} 2 \frac{\sum y_t p_t + \epsilon}{\sum y_t + \sum p_t + \epsilon}$$

FIG. 4B (L₁ SDM + Dice)

(SDM)

(Dice)

(GT)

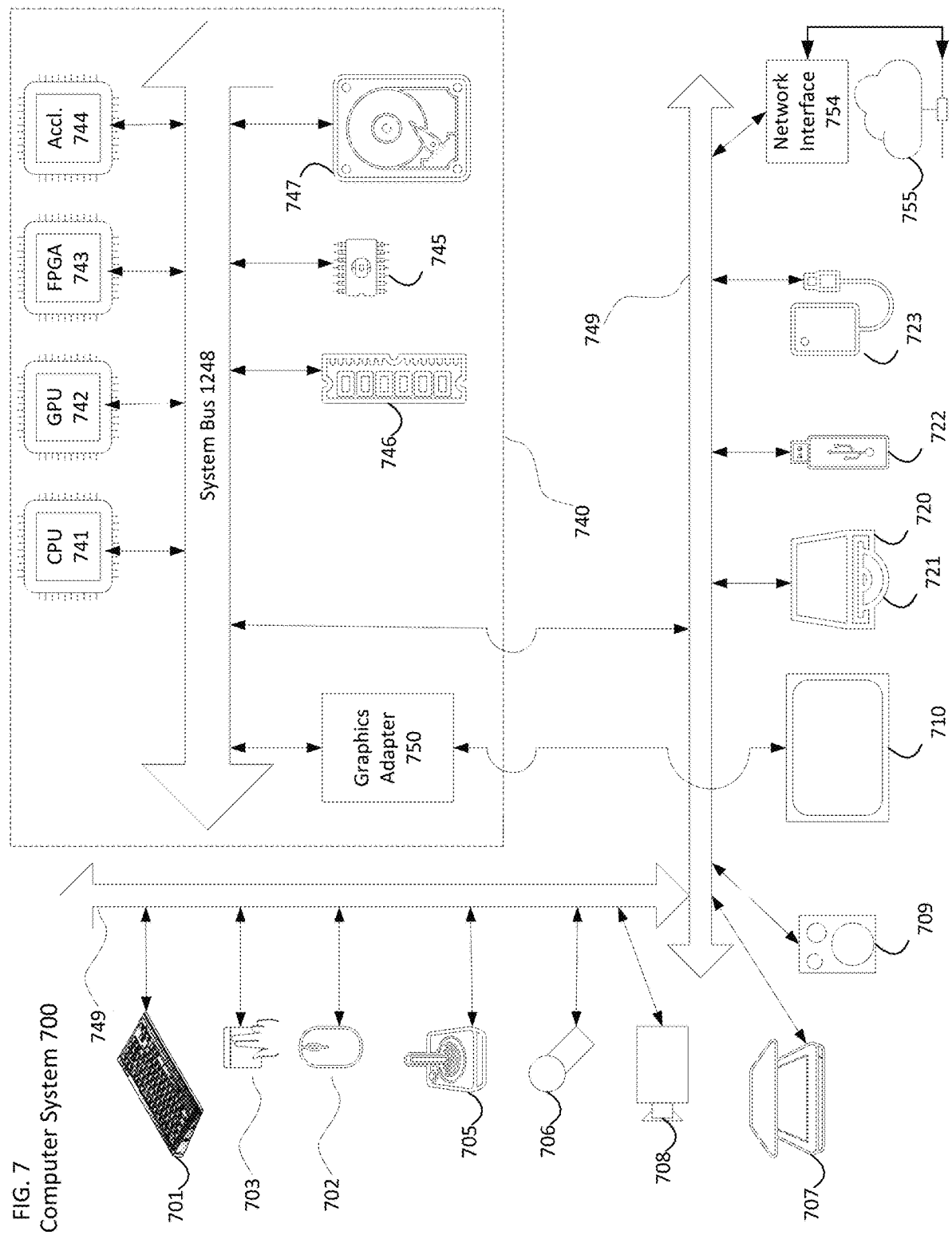

SHAPE-AWARE ORGAN SEGMENTATION BY PREDICTING SIGNED DISTANCE MAPS

BACKGROUND

Field

This disclosure is related to computer vision (e.g., object detection (identifying objects in images and video)) and artificial intelligence. In particular, the disclosure is related to using an AI neural network to perform organ segmentation for use in medical imaging technology, such as, computed tomography (CT) scans (generating digital x-ray images using x-ray beams aimed at portions of a patient (e.g., organs)). The generated digital x-ray images may be cross-sectional images of the body (or an organ of the body), which may be referred to as slices.

For surgery (e.g., organ transplant surgery), organ segmentation can be performed using a shape-aware neural network (incorporating shape knowledge of one or more organs via a statistical shape model used in the segmentation).

Listing of Related Art

Non-Patent Literature 1: Scher, A. I.; Xu, Y.; Korf, E., White, L. R.; Scheltens, P.; Toga, A. W.; Thompson, P. M.; Hartley, S.; Witter, M.; Valentino, D. J.; et al. "Mar. 12, 2007. "Hippocampal Shape Analysis in Alzheimers Disease: A Population-Based Study." Neuroimage"; 2007 May 15; 36(1):8-18. Epub 2007 Mar. 12.

Non-Patent Literature 2: Moore, K. L.; Brame, R. S.; Low, D. A.; and Mutic, S.; 2011. "Experience-Based Quality Control of Clinical Intensity Modulated Radiotherapy Planning." International Journal of Radiation Oncology* Biology* Physics 81(2):545-551.

Non-Patent Literature 3: Kass, M.; Witkin, A.; and Terzopoulos, D. 1988. "Snakes: Active Contour Models. IJCV 1(4):321-331.

Non-Patent Literature 4: Osher, S., and Sethian, J. A.; 1988. "Fronts Propagating with Curvature-Dependent speed: Algorithms based on Hamilton-Jacobi formulations." Journal of computational physics 79(1):12-49.

Non-Patent Literature 5: Cerrolaza, J. J.; Summers, R. M.; Gonz'alez Ballester, M. A'.; and Linguraru, M. G.; 2015 "Automatic Multi-Resolution Shape Modeling."

Non-Patent Literature 6: Aljabar, P.; Heckemann, R. A.; Hammers, A.; Hajnal, J. V.; and Rueckert, D; 2009; "Multi-Atlas Based Segmentation of Brain Images: Atlas Selection and Its Effect On Accuracy"; Neuroimage 46(3):726-738.

Non-Patent Literature 7: Ronneberger, O.; Fischer, P.; and Brox, T.; 2015; U-Net: Convolutional Networks for Biomedical Image Segmentation; Medical Image Computing and Computer Assisted Intervention (In MICCAI, 234-241; Springer).

Non-Patent Literature 8: Çi çek, O.; Abdulkadir, A.; Lienkamp, S. S.; Brox, T.; and Ronneberger, O.; 2016. "3d U-Net: Learning Dense Volumetric Segmentation from Sparse Annotation"; (In MICCAI, 424-432; Springer).

Non-Patent Literature 9: Kamnitsas, K.; Ledig, C.; Newcombe, V. F.; Simpson, J. P.; Kane, A. D., Menon, D. K.; Rueckert, D.; and Glocker, B., 2017; "Efficient Multi-Scale 3d CNN With Fully Connected CRF For Accurate Brain Lesion Segmentation"; MedIA 36:61-78.

Non-Patent Literature 10: Kohlberger, T.; Sofka, M.; Zhang, J.; Birkbeck, N.; Wetzl, J.; Kaftan, J.; Declerck, J.; and Zhou, S. K.; 2011; "Automatic Multi-Organ Segmentation Using Learning-Based Segmentation And Level Set Optimization"; (In MICCAI, 338-345; Springer).

Non-Patent Literature 11: Perera, S.; Barnes, N.; He, X.; Izadi, S.; Kohli, P.; and Glocker, B.; 2015; "Motion Segmentation Of Truncated Ssigned Distance Function Based Volumetric Surfaces"; (In WACV, 1046-1053. IEEE).

Non-Patent Literature 12: Hu, P.; Shuai, B.; Liu, J.; and Wang, G.; 2017; "Deep Level Sets for Salient Object Detection"; (In CVPR, 2300-2309).

Non-Patent Literature 13: Park, J. J.; Florence, P.; Straub, J.; Newcombe, R.; and Lovegrove, S.; 2019; "Deepsdf: Learning Continuous Signed Distance Functions For Shape Representation"; arXiv preprint arXiv:1901.05103.

Non-Patent Literature 14: Al Arif, S. M. R.; Knapp, K.; and Slabaugh, G.; 2018; "Spnet: Shape Prediction Using a Fully Convolutional Neural Network"; (In MICCAI, 430-439; Springer).

Non-Patent Literature 15: Dangi, S.; Yaniv, Z.; and Linte, C.; 2019; "A Distance Map Regularized CNN For Cardiac Cine MR Image Segmentation"; arXiv preprint arXiv: 1901.01238.

Non-Patent Literature 16: Navarro, F.; Shit, S.; Ezhov, I.; Paetzold, J.; Gafita, A.; Peeken, J. C.; Combs, S. E.; and Menze, B. H.; 2019; "Shape-Aware Complementary-Task Learning For Multi-Organ Segmentation"; (In MIDL, 620-627; Springer).

Non-Patent Literature 17: Wu, Y., and He, K.; 2018; "Group Normalization"; (In ECCV, 3-19).

DESCRIPTION OF RELATED ART

Organ Segmentation

In medical image segmentation, organ segmentation is of great importance in disease diagnosis and surgical planning. For instance, the segmented shape of an organ (e.g., a hippocampus) may be useful as a biomarker for neurodegenerative disorders including Alzheimer's disease (AD). See Non-Patent Literature 1.

In radiotherapy planning, accurate segmentation result of organs at risks (OARs) may help oncologists design better radiation treatment plans such as the appropriate beam paths so that radiation concentrates on the tumor region while minimizes the dose to surrounding healthy organs. See Non-Patent Literature 2.

Different from general segmentation problems such as lesion segmentation, organs have relatively stable positions, shapes and sizes. While current state-of-the-art organ segmentation systems are dominated by deep learning-based methods (Roth et al. 2015), they often lack awareness of the feasible shape and suffer from non-smoothness of the training ground truth labelled by doctors, especially in three-dimensional (3D) scenarios. See, e.g., FIG. 5A.

For organ segmentation, traditional methods include statistical models (Non-Patent Literature 5), atlas-based methods (Non-Patent Literature 6), active contour models (Non-Patent Literature 3) and level sets (Non-Patent Literature 4). The segmentation performances of atlas-based methods often rely on the accuracy of registration and label fusion algorithms. Snakes and level sets require iterative optimization through gradient descent during the inference. On the contrary, advances in deep learning based 2D (Non-Patent Literature 7) and 3D (Non-Patent Literature 8) segmentation methods have enabled more efficient and accurate organ segmentation.

Problem(s) to be Solved

Although learning based methods have faster inference speed and higher accuracy than traditional methods, they often lack awareness of anatomical shape of the target organ.

Regardless of the network architecture and training loss, the segmentation output in the related art may contain inconsistent regions and may not preserve the anatomical shape of the organ.

As a result, post-processing is required for error correction to refine the segmentation results such as CRF (Non-Patent Literature 9) or level set (Non-Patent Literature 10) to increase smoothness of the segmentation surface.

SUMMARY

According to an aspect of the disclosure, a computer-implemented method of training a neural network for organ segmentation may include: collecting a set of digital sample images from a database; inputting the collected set of digital images into a neural network recognition model; and training the neural network recognition model to recognize a first object in a first digital image as a specific object based on the first object being similar to a second object in a second digital image.

The computer-implemented method may comprise predicting a signed distance map (SDM) in conjunction with a segmentation map.

The predicting organ segmentation may be with a smooth surface and may remove noise segmentation directly without post-processing.

The method may further include connecting the segmentation map and the SDM by a differentiable approximated Heaviside function and predicting the SDM in conduction with the segmentation map as a whole.

The training may include connecting two outputs of the neural network recognition model through the differentiable approximated Heaviside function and training jointly.

The method may further include obtaining a real world captured image; inputting the captured image into the trained neural network recognition model as an input; and outputting segmentation prediction data including at least one segmented organ from the trained neural network recognition model as output, wherein the trained neural network recognition model recognizes a target real world organ.

The neural network recognition model may be a deep three-dimensional (3D) U-net.

The computer-implemented method may further include modifying the 3D U-net by performing at least one of: (A) using downsampling in the decoder and corresponding upsampling in the decoder, (B) using group normalization instead of batch normalization since, and (C) using leaky Rectified Linear Unit (ReLU) instead of ReLU as an activation function.

The modifying may include each of (A)-(C) listed above.

A graphics processing unit (GPU) may be used for performing the processing of the neural network recognition model.

The computer-implemented method may further comprise predicting, by the 3D Unet, the SDM of an organ mask.

The computer-implemented method may further comprise: after the 3D Unet predicts the SDM of the organ mask, converting the SDM of the organ mask into a segmentation mask using a Heaviside function.

The training may include training the neural network by optimizing the segmentation mask and the SDF together.

A regression loss for the SDM prediction may have two parts. A first part of the loss may minimize a difference between the predicted SDF and the groundtruth SDF. A second part of the loss may maximize the Dice similarity coefficient between the predicted mask and the groundtruth mask. A segmentation map and the distance map may be predicted in same branches, thereby guaranteeing a correspondence between the segmentation and an SDM branch.

The first part of the loss may be determined by combining a common loss used in regression tasks with a regression loss based on a product that is defined based on a formula that uses a groundtruth SDM and the predicted SDM.

The second part of the loss may be defined as a constant minus the Dice similarity coefficient.

According to an embodiment, an apparatus may comprise: at least one memory configured to store computer program code, and at least one processor configured to access the at least one memory and operate according to the computer program code.

The computer program code may comprise: collecting code configured to cause the at least one processor to collect a set of digital sample images from a database; inputting code configured to cause the at least one processor to input the collected set of digital images into a neural network recognition model; and training code configured to cause the at least one processor to train the neural network recognition model to recognize a first object in a first digital image as a specific object based on the first object being similar to a second object in a second digital image, including predicting a signed distance map (SDM) in conjunction with a segmentation map.

The collecting may include obtaining a real world captured image.

The inputting may include inputting the captured image into the trained neural network recognition model as an input.

The computer program code may further include outputting code configured to cause the at least one processor to output segmentation prediction data including at least one segmented organ from the trained neural network recognition model as output.

The trained neural network recognition model may recognize a target real world organ.

The neural network recognition model may be a deep three-dimensional (3D) U-net.

The training may include modifying the 3D U-net by performing at least one of: (A) using downsampling in the decoder and corresponding upsampling in the decoder, (B) using group normalization instead of batch normalization since, and (C) using leaky Rectified Linear Unit (ReLU) instead of ReLU as an activation function.

The outputting may include: predicting, by the 3D Unet, the SDM of an organ mask, and after the 3D Unet predicts the SDM of the organ mask, converting the SDM of the organ mask into a segmentation mask using a Heaviside function.

The training may include training the neural network by optimizing the segmentation mask and the SDF together.

A regression loss for the SDM prediction may have two parts, a first part of the loss minimizes a difference between the predicted SDF and the groundtruth SDF, and the second part maximizes the Dice similarity coefficient between the predicted mask and the groundtruth mask, wherein segmentation map and the distance map are predicted in same branches, thereby guaranteeing a correspondence between the segmentation and an SDM branch.

According to an embodiment, a non-transitory computer-readable storage medium storing instructions may be provided. The instruction may cause one or more processors to: collect a set of digital sample images from a database; input the collected set of digital images into a neural network recognition model; and train the neural network recognition model to recognize a first object in a first digital image as a specific object based on the first object being similar to a second object in a second digital image, including predicting a signed distance map (SDM) in conjunction with a segmentation map.

BRIEF DESCRIPTION OF THE DRAWINGS

Further features, the nature, and various advantages of the disclosed subject matter will be more apparent from the following detailed description and the accompanying drawings in which:

FIG. 4A shows a formula for calculating a regression loss according to an embodiment.

FIG. 4B shows a formula for calculating a Dice loss part according to an embodiment.

FIGS. 5A-5C show example hippocampus segmentation comparison of: (FIG. 5A) groundtruth annotation, (FIG. 5B) segmentation result from the model without predicting the signed distance map; and (FIG. 5C) segmentation result from the model with predicting the signed distance map.

FIG. 7 is a schematic illustration of a computer system in accordance with an embodiment.

DETAILED DESCRIPTION

Techniques for organ segmentation can be implemented by one or more processors that may execute computer software having computer-readable instructions (code) that may be physically stored in one or more computer-readable media (e.g., a hard disk drive). For example, FIG. 7, which is discussed in detail below, shows a computer system 700 suitable for implementing certain embodiments of the disclosed subject matter.

In conventional medical image segmentation methods, a smoothness issue can be mitigated by adding a regularization term with physical meaning, such as in, for example, snakes (Non-Patent Literature 3) and level sets (Non-Patent Literature 4).

To leverage the shape awareness of traditional methods, according to an embodiment, the Inventors propose to regress the Signed Distance Function (SDF) directly from the input images through a 3D convolutional neural network.

Signed Distance Map

Several works have explored the applications of a Signed Distance Map (SDM) or Signed Distance Function (SDF) in computer vision and graphics technological areas. See, e.g., Non-Patent Literature 11, which uses a truncated SDF to better reconstruct volumetric surfaces on RGB-D images. Non-Patent Literature 12 treats the linearly shifted saliency map as the SDF and refines the predicted saliency map in multiple training stages with level set smoothness terms.

Non-Patent Literature 13 learns the continuous 3D SDF directly from point samples by a network containing series of fully connected layers and an L1 regression loss.

The learned SDFs may be used for obtaining state-of-the-art shape representation and completion results. Since medical images contain richer contextual information than point samples, more sophisticated network architecture and training strategy needs to be considered when applying SDM learning on organ segmentation tasks.

Non-Patent Literature 14 proposes to use a distance map (not signed) as an intermediate step for 2D organ shape prediction task. The conversion from distance map to shape parameter vector is done by a PCA and the segmentation map is not involved.

However, for 3D organ segmentation with much higher dimensionality than 2D cases, directly applying the method of Non-Patent Literature 14 may not work well in small organs.

More recently, Non-Patent Literatures 15 and 16 use distance map prediction as a regularizer during training for organ segmentation.

Because Non-Patent Literatures 15 and 16 predict segmentation map and distance map in different branches, the correspondence between the segmentation and the SDM branch are not guaranteed.

In view of the problems with the conventional technology, a new segmentation deep learning scheme and new loss to learn organ segmentation is provided according to an embodiment. According to an embodiment, the segmentation scheme is able to predict organ segmentation with a smooth surface and less noise segmentation directly without any post processing.

Figure 1:
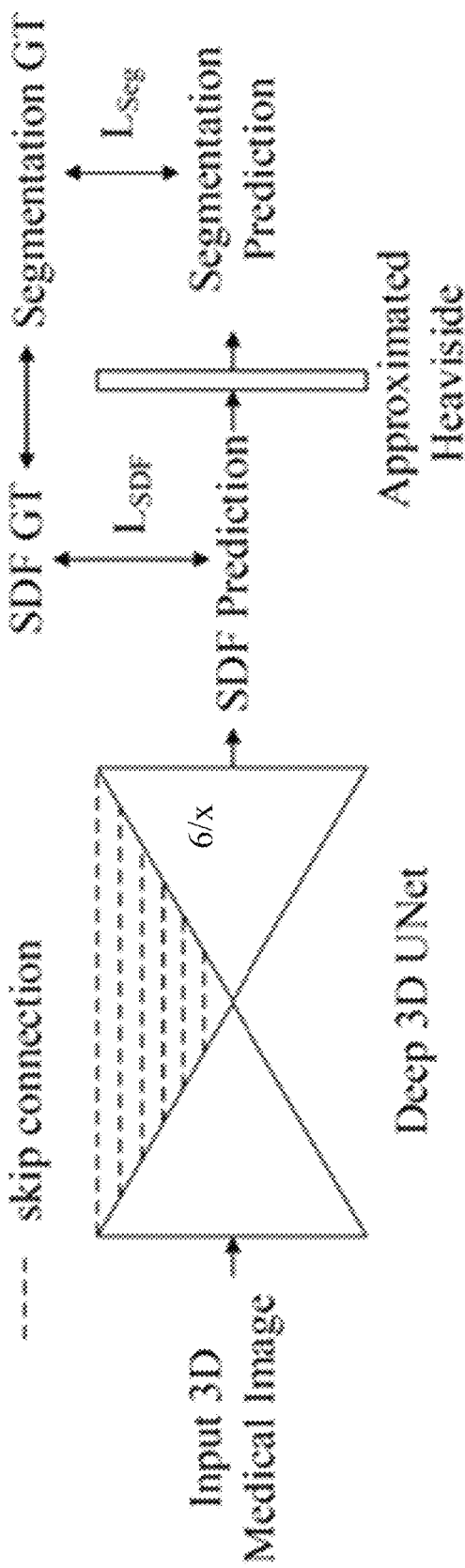
FIG. 1 is a schematic illustration of a network system architecture including an SDM learning model for organ segmentation according to an embodiment.

As shown in FIG. 1, according to an embodiment, the SDM (via SDF prediction) may be predicted in conjunction with the segmentation map instead of being a regularizer in organ segmentation tasks.

According to an embodiment, two outputs may be connected through a differentiable Heaviside function and trained jointly. According to an embodiment, a new regression loss which leads to larger gradient magnitudes for inaccurate predictions and shows better performances compared with L1 regression loss in ablation studies may be utilized.

Thus, the method according to an embodiment may differ from the method of Non-Patent Literature 14 and 15. For example, according to an embodiment, the segmentation map and SDM may be connected by a differentiable Heaviside function and can be predicted as a whole.

FIG. 1 shows a network system architecture including an SDM learning model for organ segmentation according to an embodiment.

As shown in FIG. 1, according to an embodiment, an image (e.g., a 3D medical image) may be used as input for the Deep 3D Unet (or U-net) neural network, and segmentation prediction, which may include detected objects, such as, organs), may be output.

According to an embodiment shown in FIG. 1, during training, a differentiable approximated Heaviside function may be used to train a proposed backbone deep 3D UNet by SDM loss and segmentation loss.

According to an embodiment, the 3D Unet (or U-net) may be modified. For example, as shown in FIG. 1, modifications may include one or more of: (1) using 6 downsampling in the decoder and 6 corresponding upsampling in the decoder, (2) using group normalization (e.g., group normalization similar to Non-Patent Literature 17) instead of batch normalization since, according to an embodiment, the batch size may be limited to one due to the limited size of GPU memory, (3) using leaky Rectified Linear Unit (ReLU) instead of ReLU as an activation function.

According to an embodiment, the 3D UNet may predict the SDM of the organ mask. According to an embodiment, the 3D Unet may be a model that is performed by a specialized processor, such as, a GPU, which may have limited memory.

According to an embodiment, after the 3D Unit predicts the SDM of the organ mask, a Heaviside function (e.g., similar to Non-Patent Literature 4) may be used to convert the SDM into the segmentation mask.

Figure 3:
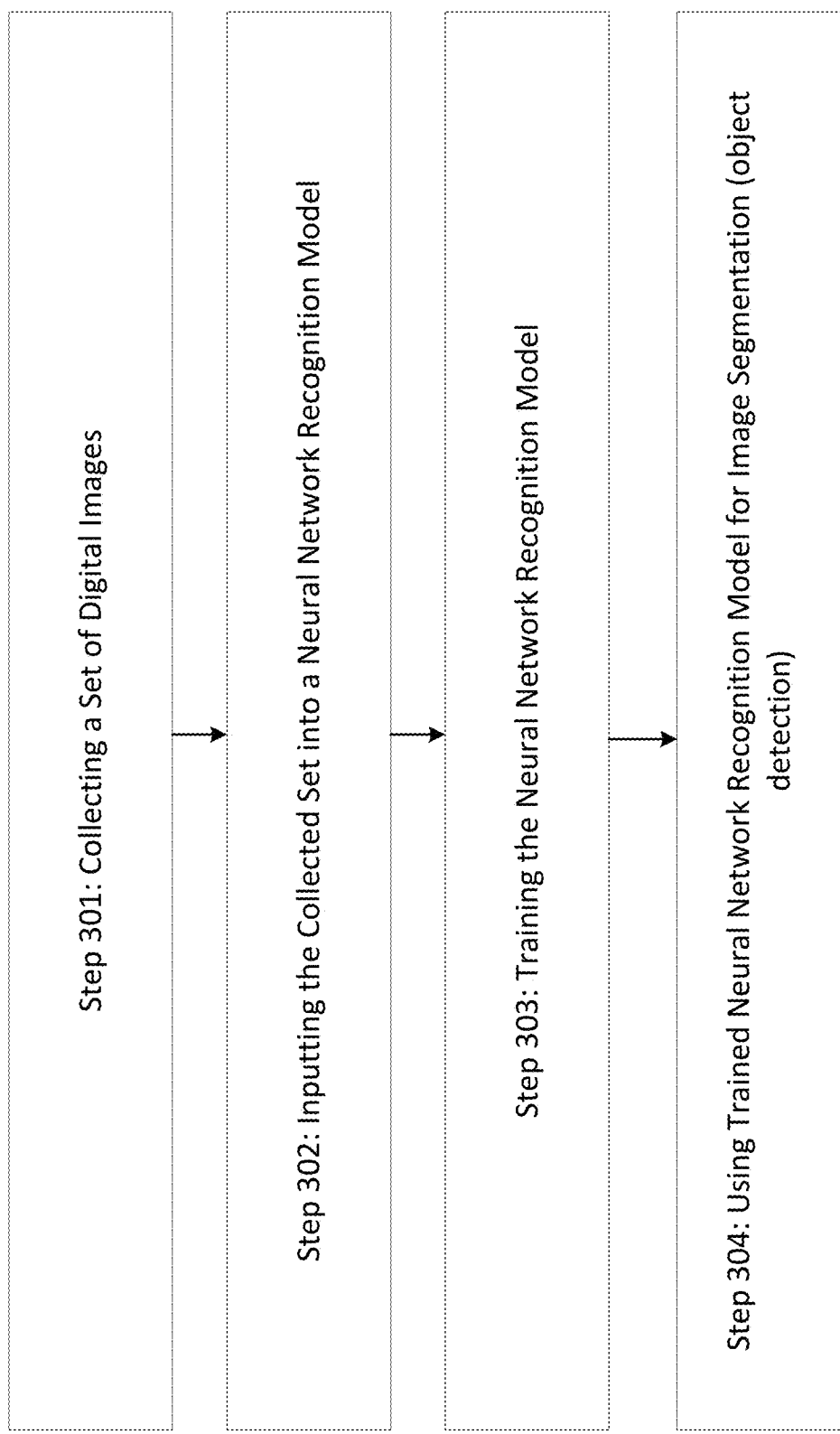
FIG. 3 shows a flowchart that may be performed by the computer system of FIG. 7, according to an aspect of the disclosure, including a computer-implemented method of training a neural network for organ segmentation.

As shown in FIG. 3, which is a flowchart that may be performed by the computer system of FIG. 7, according to an aspect of the disclosure, a computer-implemented method of training a neural network for organ segmentation may include: collecting a set of digital sample images from a database (Step 301); inputting the collected set of digital images into a neural network recognition model (Step 301); and training the neural network recognition model (Step 303).

According to an embodiment, Step 303 may include training the neural network recognition model to recognize a first object in a first digital image as a specific object based on the first object being similar to a second object in a second digital image.

The computer-implemented method may comprise predicting a signed distance map (SDM) in conjunction with a segmentation map.

The predicting organ segmentation may be with a smooth surface and may remove noise segmentation directly without post-processing.

The method may further include connecting the segmentation map and the SDM by a differentiable approximated Heaviside function and predicting the SDM in conduction with the segmentation map as a whole.

The training may include connecting two outputs of the neural network recognition model through the differentiable approximated Heaviside function and training jointly.

The method may further include obtaining a real world captured image; inputting the captured image into the trained neural network recognition model as an input; and outputting segmentation prediction data including at least one segmented organ from the trained neural network recognition model as output, wherein the trained neural network recognition model recognizes a target real world organ.

The neural network recognition model may be a deep three-dimensional (3D) U-net.

The computer-implemented method may further include modifying the 3D U-net by performing at least one of: (A) using downsampling in the decoder and corresponding upsampling in the decoder, (B) using group normalization instead of batch normalization since, and (C) using leaky Rectified Linear Unit (ReLU) instead of ReLU as an activation function.

The modifying may include each of (A)-(C) listed above.

A graphics processing unit (GPU) may be used for performing the processing of the neural network recognition model.

The computer-implemented method may further comprise predicting, by the 3D Unet, the SDM of an organ mask.

The computer-implemented method may further comprise: after the 3D Unet predicts the SDM of the organ mask, converting the SDM of the organ mask into a segmentation mask using a Heaviside function.

The training may include training the neural network by optimizing the segmentation mask and the SDF together.

A regression loss for the SDM prediction may have two parts. A first part of the loss may minimize a difference between the predicted SDF and the groundtruth SDF. A second part of the loss may maximize the Dice similarity coefficient between the predicted mask and the groundtruth mask. A segmentation map and the distance map may be predicted in same branches, thereby guaranteeing a correspondence between the segmentation and an SDM branch.

The first part of the loss may be determined by combining a common loss used in regression tasks with a regression loss based on a product that is defined based on a formula that uses a groundtruth SDM and the predicted SDM.

The second part of the loss may be defined as a constant minus the Dice similarity coefficient.

According to an embodiment, an apparatus may comprise: at least one memory configured to store computer program code, and at least one processor configured to access the at least one memory and operate according to the computer program code.

The computer program code may comprise: collecting code configured to cause the at least one processor to collect a set of digital sample images from a database; inputting code configured to cause the at least one processor to input the collected set of digital images into a neural network recognition model; and training code configured to cause the at least one processor to train the neural network recognition model to recognize a first object in a first digital image as a specific object based on the first object being similar to a second object in a second digital image, including predicting a signed distance map (SDM) in conjunction with a segmentation map.

The collecting may include obtaining a real world captured image.

The inputting may include inputting the captured image into the trained neural network recognition model as an input.

The computer program code may further include outputting code configured to cause the at least one processor to output segmentation prediction data including at least one segmented organ from the trained neural network recognition model as output.

The trained neural network recognition model may recognize a target real world organ.

The neural network recognition model may be a deep three-dimensional (3D) U-net.

The training may include modifying the 3D U-net by performing at least one of: (A) using downsampling in the decoder and corresponding upsampling in the decoder, (B) using group normalization instead of batch normalization since, and (C) using leaky Rectified Linear Unit (ReLU) instead of ReLU as an activation function.

The outputting may include: predicting, by the 3D Unet, the SDM of an organ mask, and after the 3D Unet predicts the SDM of the organ mask, converting the SDM of the organ mask into a segmentation mask using a Heaviside function.

The training may include training the neural network by optimizing the segmentation mask and the SDF together.

A regression loss for the SDM prediction may have two parts, a first part of the loss minimizes a difference between the predicted SDF and the groundtruth SDF, and the second part maximizes the Dice similarity coefficient between the predicted mask and the groundtruth mask, wherein segmentation map and the distance map are predicted in same branches, thereby guaranteeing a correspondence between the segmentation and an SDM branch.

According to an embodiment, a non-transitory computer-readable storage medium storing instructions may be provided. The instruction may cause one or more processors to: collect a set of digital sample images from a database; input the collected set of digital images into a neural network recognition model; and train the neural network recognition model to recognize a first object in a first digital image as a specific object based on the first object being similar to a second object in a second digital image, including predicting a signed distance map (SDM) in conjunction with a segmentation map.

According to an embodiment, the neural network may be trained by optimizing the segmentation mask and SDF together.

According to an embodiment, the loss may have two parts. According to an embodiment, a first part of the loss may minimize a difference between the predicted SDF and the groundtruth SDF, and the second part may maximize the Dice (coefficient) between the predicted mask the and groundtruth mask.

Figures 2A, 2B:
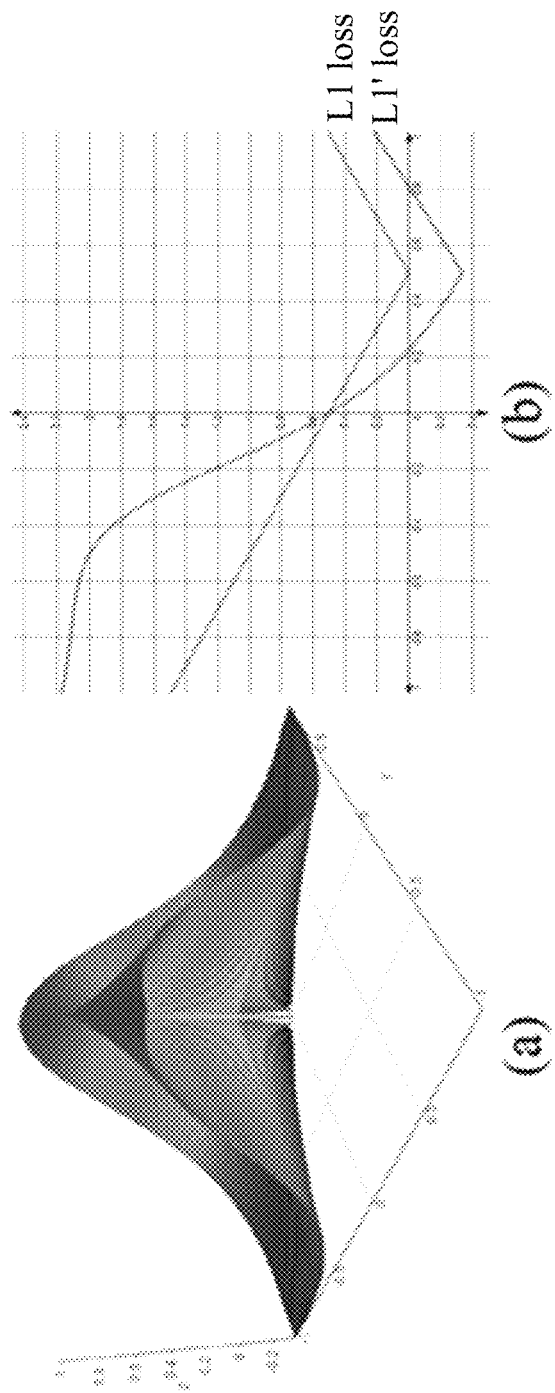
FIG. 2A shows a proposed regression loss for SDM prediction, according to an embodiment.
FIG. 2B shows, according to an embodiment, a plot of a loss value.

FIG. 2A shows a proposed regression loss for SDM prediction, according to an embodiment. According to an embodiment, all SDM values may be normalized.

FIG. 2B shows, according to an embodiment, a plot of a loss value given a ground truth SDM value of 0:5. In FIG. 2B, the Line L1' may represent a combination of a proposed loss according to an embodiment of the disclosure and the L1 loss.

According to an embodiment of the disclosure, the SDM loss part may be formularized as a regression problem. According to an embodiment, the L1 loss is a common loss used in regression tasks. However, for multi-organ segmentation tasks, training by L1 loss sometimes leads to unstable training process.

To overcome the shortcoming of L1 loss, according to an embodiment, an L1' loss may be determined by combining the L1 loss with a proposed regression loss based on a product that is defined based on a formula. For example, according to an embodiment, the regression loss may be calculated based on the formula of FIG. 4A, where $y_t$ represents the groundtruth SDM and $p_t$ denotes the predicted SDM.

According to an embodiment, taking the product of prediction and ground truth may penalize the output SDM for having the wrong sign.

According to an embodiment, for the Dice loss part, the loss may be defined as a constant minus the Dice similarity coefficient. For example, the Dice loss part may be calculated based on the formula of FIG. 4B, where N is the number of classes, t denotes the $t_{th}$ organ class. $y_t$ and $p_t$ represent the groundtruth annotation and model prediction, respectively ($\varepsilon$ may be a term with small value to avoid numerical issues).

While current state-of-the-art organ segmentation systems are dominated by deep learning-based methods (Roth et al. 2015), they often lack awareness of the feasible shape and suffer from non-smoothness of the training ground truth labelled by doctors, especially in three-dimensional (3D) scenarios. As an example, a ground truth label of a hippocampus may not maintain consistent and continuous shape due to the fact that it is annotated in two-dimensional (2D) slices by contours instead of 3D surfaces. See, e.g., FIG. 5A.

Figure 5C:
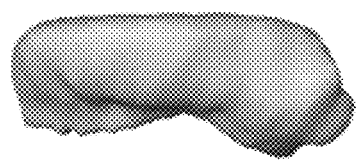
Figure 5B:
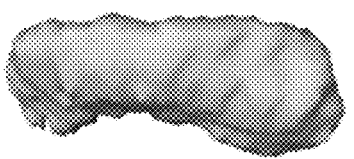
Figure 5A:
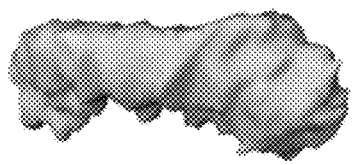

FIGS. 5A-5C show an example hippocampus segmentation comparison of: (FIG. 5A) groundtruth annotation, which lacks smoothness in 3D view due to the inconsistency of annotation in 2D; (FIG. 5B) segmentation result from the model without predicting the signed distance map; and (FIG. 5C) segmentation result from the model with predicting the signed distance map, which is clearly smoother than FIGS. 5A and 5B while preserving the overall shape.

FIG. 1 shows an exemplary flow of an embodiment according to the disclosure.

According to an embodiment, the neural network may receive an image (e.g., a 3D medical image) as input. According to an embodiment, the neural network may output an SDF prediction. According to an embodiment, the neural network may include one or more skip connections (e.g., one or more extra connections between nodes in different layers of a neural network that skip one or more layers of nonlinear processing), as shown in FIG. 1.

According to an embodiment, the loss may have two parts. According to an embodiment, the two parts of the loss may include a first part that minimizes the difference between the predicted SDF and the groundtruth SDF, and a second part that maximizes the dice between the predicted mask the and groundtruth mask.

FIGS. 8A and 8B show the losses, according to an embodiment.

According to an embodiment, the SDM loss part may be formularized as a regression problem. According to an embodiment, an L1 loss may be a common loss used in regression tasks. However, training by L1 loss sometimes leads to unstable training process (e.g., when training for multi-organ segmentation tasks). To overcome the shortcoming of L1 loss, according to an embodiment, the L1 loss is combined with a regression loss L'. According to an embodiment, the regression Loss L' may be based on a product that is based on the formula in FIG. 4A.

According to an embodiment, the intuition behind taking the product of prediction and ground truth is to penalize the output SDM for having the wrong sign.

Figure 6E:
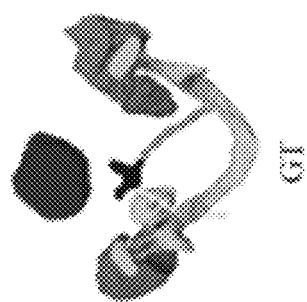
FIGS. 6A-6E show examples of output image (organ) segmentation using GT, DICE, SDM, L1 SDM+Dice and an embodiment of the present disclosure ("ours"), respectively.
Figure 6D:
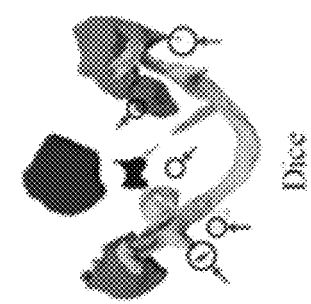
Figure 6C:
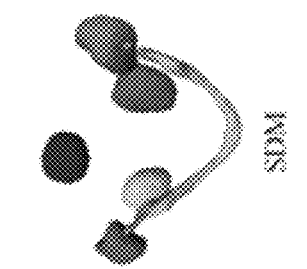
Figure 6B:
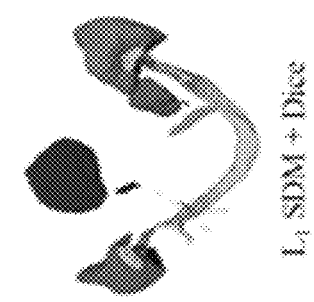
Figure 6A:
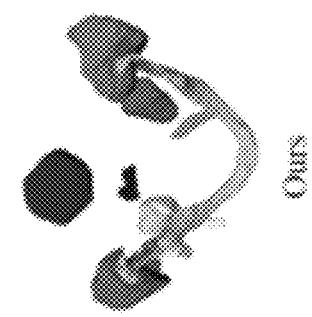

FIGS. 6A-6E show examples of output image (organ) segmentation using GT, DICE, SDM, L1 SDM+Dice and an embodiment of the present disclosure ("ours"). In particular, FIG. 6A shows GT, FIG. 6B shows Dice, FIG. 6C shows SDM, FIG. 6D shows L1 SDM+Dice, and FIG. 6E shows an embodiment of the present disclosure ("ours").

As shown in FIG. 7, the computer software can be coded using any suitable machine code or computer language, that may be subject to assembly, compilation, linking, or like mechanisms to create code comprising instructions that can be executed directly, or through interpretation, micro-code execution, and the like, by computer central processing units (CPUs), Graphics Processing Units (GPUs), and the like.

The instructions can be executed on various types of computers or components thereof, including, for example, personal computers, tablet computers, servers, smartphones, gaming devices, internet of things devices, and the like.

The components shown in FIG. 7 for computer system 700 are exemplary in nature and are not intended to suggest any limitation as to the scope of use or functionality of the computer software implementing embodiments of the present disclosure. Neither should the configuration of components be interpreted as having any dependency or requirement relating to any one or combination of components illustrated in the exemplary embodiment of a computer system 700.

Computer system 700 may include certain human interface input devices. Such as a human interface input device may be responsive to input by one or more human users through, for example, tactile input (such as: keystrokes, swipes, data glove movements), audio input (such as: voice, clapping), visual input (such as: gestures), olfactory input, etc. The human interface devices can also be used to capture certain media not necessarily directly related to conscious input by a human, such as audio (such as: speech, music, ambient sound), images (such as: CT images, scanned images, photographic images obtain from a still image camera), video (such as two-dimensional video, three-dimensional video including stereoscopic video).

Input human interface devices may include one or more of (only one of each depicted): keyboard 701, mouse 702, trackpad 703, touch screen 710, data-glove 704, joystick 705, microphone 706, scanner 707, camera 708, etc. According to an embodiment, the camera 708 may be a CT scanner. According to an embodiment, the camera 708 may be a medical imaging device.

Computer system 700 may also include certain human interface output devices. Such human interface output devices may be stimulating the senses of one or more human users through, for example, tactile output, sound, light, and smell/taste. Such human interface output devices may include tactile output devices (for example tactile feedback by the touch-screen 710, data-glove 704, or joystick 705, but there can also be tactile feedback devices that do not serve as input devices), audio output devices (such as: speakers 709, headphones (not depicted)), visual output devices (such as screens 710 to include CRT screens, LCD screens, plasma screens, OLED screens, each with or without touch-screen input capability, each with or without tactile feedback capability-some of which may be capable to output two dimensional visual output or more than three dimensional output through means such as stereographic output; virtual-reality glasses, holographic displays and smoke tanks, and printers.

Computer system 700 can also include human accessible storage devices and their associated media such as optical media including CD/DVD ROM/RW 720 with CD/DVD or the like media 721, thumb-drive 722, removable hard drive or solid state drive 723, legacy magnetic media such as tape and floppy disc (not depicted), specialized ROM/ASIC/PLD based devices such as security dongles (not depicted), and the like.

Those skilled in the art should also understand that the term "computer readable media" or "computer readable medium" as used in connection with the presently disclosed subject matter corresponds to non-transitory computer readable media and does not encompass transmission media, carrier waves, or other transitory signals.

Computer system 700 can also include interface to one or more communication networks. Networks can for example be wireless, wireline, optical. Networks can further be local, wide-area, metropolitan, vehicular and industrial, real-time, delay-tolerant, and so on. Examples of networks include local area networks such as Ethernet, wireless LANs, cellular networks to include GSM, 3G, 4G, 5G, LTE and the like, TV wireline or wireless wide area digital networks to include cable TV, satellite TV, and terrestrial broadcast TV, vehicular and industrial to include CANBus, and so forth. Certain networks commonly require external network interface adapters that attached to certain general purpose data ports or peripheral buses (749) (such as, for example USB ports of the computer system 700; others are commonly integrated into the core of the computer system 700 by attachment to a system bus as described below (for example Ethernet interface into a PC computer system or cellular network interface into a smartphone computer system). Using any of these networks, computer system 700 can communicate with other entities. Such communication can be uni-directional, receive only (for example, broadcast TV), uni-directional send-only (for example CANbus to certain CANbus devices), or bi-directional, for example to other computer systems using local or wide area digital networks. Certain protocols and protocol stacks can be used on each of those networks and network interfaces as described above.

Aforementioned human interface devices, human-accessible storage devices, and network interfaces can be attached to a core 740 of the computer system 700.

The core 740 can include one or more Central Processing Units (CPU) 741, Graphics Processing Units (GPU) 742, specialized programmable processing units in the form of Field Programmable Gate Areas (FPGA) 743, hardware accelerators for certain tasks 744, and so forth. These devices, along with Read-only memory (ROM) 745, Random-access memory 746, internal mass storage such as internal non-user accessible hard drives, SSDs, and the like 747, may be connected through a system bus 748. In some computer systems, the system bus 748 can be accessible in the form of one or more physical plugs to enable extensions by additional CPUs, GPU, and the like. The peripheral devices can be attached either directly to the core's system bus 748, or through a peripheral bus 749. Architectures for a peripheral bus include PCI, USB, and the like.

CPUs 741, GPUs 742, FPGAs 743, and accelerators 744 can execute certain instructions that, in combination, can make up the aforementioned computer code. That computer code can be stored in ROM 745 or RAM 746. Transitional data can be also be stored in RAM 746, whereas permanent data can be stored for example, in the internal mass storage 747. Fast storage and retrieve to any of the memory devices can be enabled through the use of cache memory, that can be closely associated with one or more CPU 741, GPU 742, mass storage 747, ROM 745, RAM 746, and the like.

According to an embodiment, the CPU may use one or more of the GPU, FPGA or Accelerator to perform the neural network processing.

The computer readable media can have computer code thereon for performing various computer-implemented operations. The media and computer code can be those specially designed and constructed for the purposes of the present disclosure, or they can be of the kind well known and available to those having skill in the computer software arts.

As an example and not by way of limitation, the computer system having architecture 700, and specifically the core 740 can provide functionality as a result of processor(s) (including CPUs, GPUs, FPGA, accelerators, and the like) executing software embodied in one or more tangible, computer-readable media. Such computer-readable media can be media associated with user-accessible mass storage as introduced above, as well as certain storage of the core 740 that are of non-transitory nature, such as core-internal mass storage 747 or ROM 745. The software implementing various embodiments of the present disclosure can be stored in such devices and executed by core 740. A computer-readable medium can include one or more memory devices or chips, according to particular needs. The software can cause the core 740 and specifically the processors therein (including CPU, GPU, FPGA, and the like) to execute particular processes or particular parts of particular processes described herein, including defining data structures stored in RAM 746 and modifying such data structures according to the processes defined by the software. In addition or as an alternative, the computer system can provide functionality as a result of logic hardwired or otherwise embodied in a circuit (for example: accelerator 744), which can operate in place of or together with software to execute particular processes or particular parts of particular processes described herein. Reference to software can encompass logic, and vice versa, where appropriate. Reference to a computer-readable media can encompass a circuit (such as an integrated circuit (IC)) storing software for execution, a circuit embodying logic for execution, or both, where appropriate. The present disclosure encompasses any suitable combination of hardware and software.

Advantages

1) Does not need any post processing because the direct output of the network remains smooth and free of small sparkles.

2) Any existing 3D segmentation network can be easily adapted to incorporate an SDM prediction model with nearly no additional overhead.

While this disclosure has described several exemplary embodiments, there are alterations, permutations, and various substitute equivalents, which fall within the scope of the disclosure. It will thus be appreciated that those skilled in the art will be able to devise numerous systems and methods which, although not explicitly shown or described herein, embody the principles of the disclosure and are thus within the spirit and scope thereof.

The invention claimed is:

1. A computer-implemented method of training a neural network for organ segmentation, the computer-implemented method comprising:
   collecting a set of digital sample images from a database;
   inputting the collected set of digital sample images into a neural network recognition model;
   training the neural network recognition model to recognize a first object in a first digital sample image as a specific object based on the first object being similar to a second object in a second digital sample image, wherein the computer-implemented method comprises predicting a signed distance map (SDM) in conjunction with a segmentation map; and
   connecting the segmentation map and the SDM by a differentiable approximated Heaviside function and predicting the SDM in conduction with the segmentation map as a whole, wherein the training includes connecting two outputs of the neural network recognition model through the differentiable approximated Heaviside function and training jointly.

2. The computer-implemented method of claim 1, further comprising:
   predicting organ segmentation with a smooth surface and removing noise segmentation directly without post-processing.

3. The computer-implemented method of claim 1, further comprising:
   obtaining a real world captured image;
   inputting the captured image into the trained neural network recognition model as an input; and
   outputting segmentation prediction data including at least one segmented organ from the trained neural network recognition model as output, wherein the trained neural network recognition model recognizes a target real world organ.

4. The computer-implemented method of claim 1, wherein the neural network recognition model is a deep three-dimensional (3D) U-net.

5. The computer-implemented method of claim 4, further comprising modifying the 3D U-net by performing at least one of: (A) using downsampling in a decoder and corresponding upsampling in the decoder, (B) using group normalization instead of batch normalization since, and (C) using leaky Rectified Linear Unit (ReLU) instead of ReLU as an activation function.

6. The computer-implemented method of claim 1, wherein a graphics processing unit (GPU) is used for performing the processing of the neural network recognition model.

7. The computer-implemented method of claim 4, further comprising, predicting, by the 3D Unet, the SDM of an organ mask.

8. The computer-implemented method of claim 7, further comprising: after the 3D Unet predicts the SDM of the organ mask, converting the SDM of the organ mask into a segmentation mask using a Heaviside function.

9. The computer-implemented method of claim 8, wherein the training includes training the neural network by optimizing the segmentation mask and a Signed Distance Function (SDF) together.

10. The computer-implemented method of claim 9, wherein a regression loss for the SDM prediction has two parts, a first part of the regression loss minimizes a difference between the predicted SDF and a groundtruth SDF, and a second part of the regression loss maximizes a Dice similarity coefficient between a predicted mask and a groundtruth mask, wherein the segmentation map and a distance map are predicted in same branches, thereby guaranteeing a correspondence between the segmentation and an SDM branch.

11. The computer-implemented method of claim 10, wherein the first part of the regression loss is determined by combining a common loss used in regression tasks with a regression loss based on a product that is defined based on a formula that uses a groundtruth SDM and the predicted SDM.

12. The computer-implemented method of claim 10, wherein the second part of the regression loss is defined as a constant minus the Dice similarity coefficient.

13. An apparatus comprising:
   at least one memory configured to store computer program code; and
   at least one processor configured to access the at least one memory and operate according to the computer program code, the computer program code comprising:
      collecting code configured to cause the at least one processor to collect a set of digital sample images from a database;
      inputting code configured to cause the at least one processor to input the collected set of digital sample images into a neural network recognition model;
      training code configured to cause the at least one processor to train the neural network recognition model to recognize a first object in a first digital sample image as a specific object based on the first object being similar to a second object in a second digital sample image, including predicting a signed distance map (SDM) in conjunction with a segmentation map; and connecting code configured to cause the at least one processor to connect the segmentation map and the SDM by a differentiable approximated Heaviside function and predicting the SDM in conduction with the segmentation map as a whole, wherein the training by the training code includes connecting two outputs of the neural network recognition model through the differentiable approximated Heaviside function and training jointly.

14. The apparatus of claim 13, wherein the collecting includes obtaining a real world captured image;

the inputting includes inputting the captured image into the trained neural network recognition model as an input; and the computer program code includes outputting code configured to cause the at least one processor to output segmentation prediction data including at least one segmented organ from the trained neural network recognition model as output, wherein the trained neural network recognition model recognizes a target real world organ.

15. The apparatus of claim 13, wherein the neural network recognition model is a deep three-dimensional (3D) U-net.

16. The apparatus of claim 15, wherein the training includes modifying the 3D U-net by performing at least one of: (A) using downsampling in a decoder and corresponding upsampling in the decoder, (B) using group normalization instead of batch normalization since, and (C) using leaky Rectified Linear Unit (ReLU) instead of ReLU as an activation function.

17. The apparatus of claim 15, wherein the outputting includes:

predicting, by the 3D Unet, the SDM of an organ mask, and after the 3D Unet predicts the SDM of the organ mask, converting the SDM of the organ mask into a segmentation mask using a Heaviside function.

18. The apparatus of claim 17, wherein the training includes training a neural network by optimizing the segmentation mask and the SDF together, and a regression loss for the SDM prediction has two parts, a first part of the regression loss minimizes a difference between the predicted SDF and a groundtruth SDF, and a second part of the regression loss maximizes a Dice similarity coefficient between a predicted mask and a groundtruth mask, wherein the segmentation map and a distance map are predicted in same branches, thereby guaranteeing a correspondence between the segmentation and an SDM branch.

19. A non-transitory computer-readable storage medium storing instructions that cause one or more processors to:

collect a set of digital sample images from a database;

input the collected set of digital sample images into a neural network recognition model;

train the neural network recognition model to recognize a first object in a first digital sample image as a specific object based on the first object being similar to a second object in a second digital sample image, including predicting a signed distance map (SDM) in conjunction with a segmentation map; and connecting the segmentation map and the SDM by a differentiable approximated Heaviside function and predicting the SDM in conduction with the segmentation map as a whole, wherein training the neural network recognition model includes connecting two outputs of the neural network recognition model through the differentiable approximated Heaviside function and training jointly.

* * * * *